(12) United States Patent
Hekimian

(10) Patent No.: US 7,445,447 B2
(45) Date of Patent: Nov. 4, 2008

(54) METHOD AND SYSTEM FOR VERIFYING THE USE OF ORTHODONTIC ELASTIC BANDS

(76) Inventor: Christopher David Hekimian, 13416 Rising Sun La., Germantown, MD (US) 20874

( * ) Notice: Subject to any disclaimer, the term of this patent is extended or adjusted under 35 U.S.C. 154(b) by 8 days.

(21) Appl. No.: 11/026,240

(22) Filed: Jan. 3, 2005

(65) Prior Publication Data

US 2006/0147869 A1    Jul. 6, 2006

(51) Int. Cl.
*A61C 3/00* (2006.01)
(52) U.S. Cl. .............................. 433/18; 433/2
(58) Field of Classification Search ............ 433/13, 433/18, 2, 19
See application file for complete search history.

(56) References Cited

U.S. PATENT DOCUMENTS

| | | | |
|---|---|---|---|
| 4,818,225 A | 4/1989 | Fasnacht | |
| 4,975,051 A | 12/1990 | Kargas et al. | |
| 5,054,647 A * | 10/1991 | Yawata | 221/41 |
| 5,184,954 A | 2/1993 | Hanson | |
| 5,505,616 A * | 4/1996 | Harwell | 433/21 |
| 5,674,067 A * | 10/1997 | Masel | 433/24 |
| 5,887,719 A * | 3/1999 | Edwards | 206/534 |
| 6,203,317 B1 | 3/2001 | Davanathan | |
| 6,386,864 B1 | 5/2002 | Kuo | |
| 6,461,157 B1 | 10/2002 | Kussick | |
| 6,488,498 B1 | 12/2002 | Mariani, Jr. | |
| 6,746,243 B1 | 6/2004 | Holzhauer | |
| 2006/0068353 A1 * | 3/2006 | Abolfathi et al. | 433/6 |

* cited by examiner

*Primary Examiner*—Ralph A Lewis
(74) *Attorney, Agent, or Firm*—Liberman & Brandsdorfer, LLC

(57) ABSTRACT

An orthodontic elastic band which is dyed with a semi-persistent food-based dye such that the distinction between unused and used elastic bands is evident upon inspection is used in conjunction with a compartmented container, such as a weekly pill box. The compartmented container is used to store used orthodontic elastic bands as they are removed and replaced, before and after meals, respectively, throughout the day. Verification of the rigor with which a predefined orthodontic regimen involving replaceable elastic bands is determined based upon the inspection and count of the number of used elastic bands which have been stored in the compartment associated with each day. Missing, used elastic bands are indicative in a lapse in the prescribed elastic band regimen.

4 Claims, 2 Drawing Sheets

METHOD AND SYSTEM FOR VERIFYING THE USE OF ORTHODONTIC ELASTIC BANDS

BACKGROUND OF THE INVENTION

Apparatuses and methods consistent with the present invention relate in general to orthodontic elastic bands, and more particularly to a kind of orthodontic elastic bands which incorporate a means of verifying whether an orthodontic patient has been using the elastic bands regularly, as prescribed.

It is a challenge shared by orthodontic professionals and parents of children and young adults that are undergoing orthodontic treatment to ensure that the patients adhere to their orthodontic and dental regimen with rigor. A large proportion of individuals undergoing orthodontic treatment require the use orthodontic elastic bands at some point during their treatment. The elastic bands are used to apply force between orthodontic appliances and would be most commonly identified as small rubber bands. The elastic bands are typically awkward to install and remove and are often uncomfortable to wear. Consequently, orthodontic patients tend to be at risk of lapsing in the use of their elastic bands. Such a lapse, is typically associated with a prolongation of the total treatment interval and can therefore be very costly. The challenge is a difficult one due the discipline required of the typically younger, orthodontic patients may not be sufficient to ensure that they remove and reinstall their elastic bands before and after each meal, or as required. Furthermore, the orthodontic patients may not be paying for their treatments directly and are therefore insulated from any direct financial incentive for complying to their orthodontic treatment program with rigor.

Conventional attempts to encourage the rigorous use of orthodontic elastic bands have focused on making the elastic bands in stylish colors, or on providing them with flavor (Fasnacht, U.S. Pat. No. 4,818,225). For example, orthodontic elastic bands (which includes other removable devices which are intended to exert forces relative to orthodontic appliances) may be flavored and/or colored. Davanathan teaches a method of manufacturing elastic bands such that they have a hydrophyllic quality and have a low coefficient of friction when worn, making them more comfortable (Davanathan, U.S. Pat. No. 6,203,317). Orthodontic elastic bands may be provided in varying sizes and designs.

Although the conventional approaches noted above may tend to make the use of orthodontic elastic bands more appealing to the user, they are not without shortcomings. Namely, a need still remains to verify that an orthodontic patient has been using their elastic bands as required. Such a verification system could allow parents to avoid unnecessary orthodontic treatments and costs for those orthodontic patients in their charge through a program of verification of compliance, or could be advantageously used as a basis for establishing a positive feedback reward system. Through a program which encouraged the use of a system of verification of use of orthodontic elastic bands by orthodontic treatment providers, underwriters of orthodontic care could realize significant cost savings, limiting the effects of poor orthodontic elastic band compliance among their patients.

SUMMARY OF THE INVENTION

The invention resides in a the systematic use of elastic bands that have been dyed with a non-persistent and non-toxic dye. Used elastic bands can be distinguished from unused ones based upon a characteristic loss of pigment, due to use over the course of several hours. Dyed elastic bands which have been worn can be expected to lose pigment to a degree which depends upon how long they were worn and the wetness of the mouth. The portion of the elastic band which remains in contact with the orthodontic appliance it is attached to, will retain all or most of it's pigment.

The invention also resides a compartmented container such as a daily medication box into which each rinsed, used elastic band is stored. The length of the regimen to be verified is limited by the number of compartments that the container has, such that a seven-compartment container would be limited to verifying one weeks worth of regimen compliance assuming that one day's worth of elastic bands would fit into one compartment.

The invention also resides in a method to verify adherence to a regimen of orthodontic band use. The method involves providing elastic bands which have been dyed with a non-persistent dye and multiple compartment container to the orthodontic patient. The orthodontic patient is instructed on the correct use of the elastic bands in their overall orthodontic treatment. Furthermore, the patient is instructed to use new elastic bands after every meal, and to rinse and save each used band in the appropriate compartment of the container provided. Regimen adherence would be typically assessed after seven days for a seven compartment box or after "k" days for a "k" compartment box. In practice, a regimen of any number of days <k can be verified when a container with k compartments is used. Regimen periods of greater than k days must be verified in stages of no more than k days each. The adherence assessment process is simple and involves the counting of elastic bands (used) and verifying that each set of rubber bands exhibits the characteristic signs of wear (i.e. general loss of pigment with pigment retained only at the points of appliance application). The number of compartments within the box which do not contain a complete set of worn bands is taken to correspond to the number of days for which the elastic band regimen was incomplete. After each assessment, the used bands are disposed of such that each assessment period can be started with an empty container.

The above and other features of the invention including various and novel details of construction and process steps will now be more particularly described with reference to the accompanying drawings and pointed out in the claims. It will be understood that the particular orthodontic elastic bands, elastic band container, and method for verifying adherence to an orthodontic elastic band regimen embodying the invention is shown by way of illustration only and not as a limitation of the invention. The principles and features of this invention may be employed in varied and numerous embodiments without departing from the scope of the invention.

DETAILED DESCRIPTION OF AN ILLUSTRATIVE, NON-LIMITING EMBODIMENT OF THE INVENTION

Figure 1A:
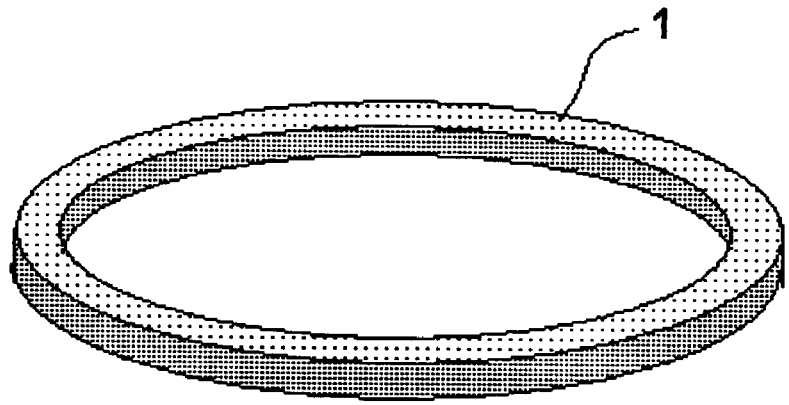
FIG. 1a is a perspective view of orthodontic elastic band without semi-persistent pigmentation.

I. The Pigmented Elastic Bands:

FIG. 1A shows the kind of elastic band that is used as a force exerting member in an orthodontic regimen 1. The elastic bands are available in different sizes and are designed to be deployed within an orthodontic patient's mouth, connecting and applying force between orthodontic appliances which are affixed to teeth. Orthodontic elastic bands interfere with mastication and must be removed before meals. The elastic bands are subject to wear and therefore are typically replaced subsequent to each meal.

Figure 1B:
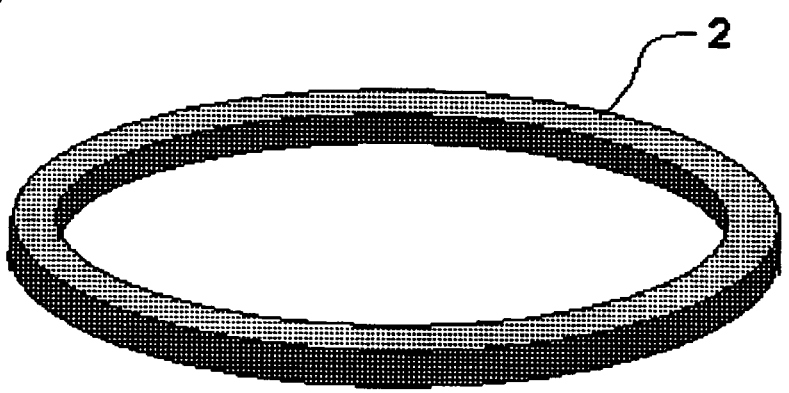
FIG. 1b is a perspective view of orthodontic elastic band with semi-persistent pigmentation prior to use, according to an illustrative, non-limiting embodiment of the present invention.

FIG. 1B represents an elastic band that has been dyed with food coloring 2. Food coloring can be obtained in a variety of colors and with varying degrees of persistence, when exposed to moisture. For the purposes of this invention, high persistent food coloring dyes are favorable so that the coloring of the bands persists for at least an hour when worn. There are a number of factors that can effect the persistence of the dye upon the elastic. Some rubbers are more receptive to colored dyes than others. Elastic bands that are not receptive to food coloring dyes can be made more receptive to the dyes by dying them while they are stretched over a form. Other factors that affect color persistence are the temperature of the dye and the length of time that the rubber is exposed to the dye. Due to the large number of variations including the type of rubber, the characteristic persistence of the dye, the state of the elastic band and the temperature and duration of the dying process, it is not practical to describe with specificity a dying process which will always be acceptable.

For a given dye and manufacturer of elastic band, a person skilled in the art of chemical dying processes, using methods discussed in paragraph 14, will be able to determine how to achieve an acceptable degree of dye persistence on the elastic bands. The goal of the dying process is to obtain a state of persistence which will allow some pigmentation to remain after the bands have been worn for at least an hour, and not to wash off easily. When removed prior to each meal, the persistence should be such that signs of wear, such as overall fading, or localized fading of the pigment should be evident. It is not generally desirable that no signs of the original pigment should remain as the bands should look used, and not like new, unpigmented bands 1.

Figure 1C:
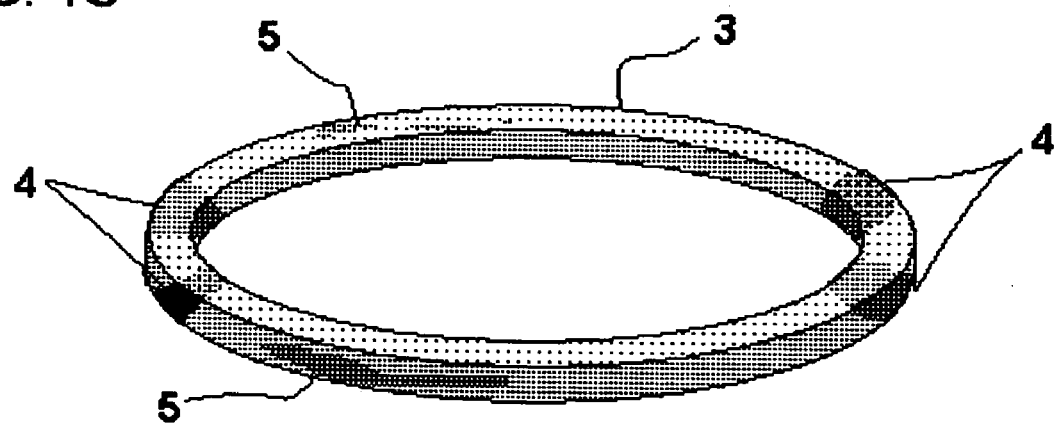
FIG. 1c is a perspective view of orthodontic elastic band with semi-persistent pigmentation subsequent to use, according to an illustrative, non-limiting embodiment of the present invention.

FIG. 1C represents an elastic band, pigmented with a semi-persistent food coloring dye, and worn in the mouth, pursuant to the new invention system 3. Generally, in practice, the worn band shown in FIG. 1C would be distinguishable from the new, undyed band 1 shown in FIG. 1A by the existence of signs of pigmentation that have not completely worn off during use. The appliance marks 4, represent such signs. Dye that exists on portions of the elastic band that were in continuous contact with orthodontic appliances are less likely to be lost to the moisture within the mouth that caused the fading of the pigment elsewhere on the band. The overall fading of the pigmentation, and remnants of the original color 5 on the used band will also distinguish the used band 3 from a new, or used, undyed band 1.

FIG. 1C would be distinguishable from the unused, dyed band 1 based upon the existence of the appliance marks 4, overall fading of the characteristic color, and remnants of the dye that were not completely worn or washed away during use 5.

The characteristic of the elastic bands that have been dyed pursuant to the new invention process, that they lose some or all of their pigment during use, or show some other, readily identifiable signs of wear, is key to the new invention for verifying adherence with an orthodontic regimen involving elastic bands.

II. The Compartmented Container

Figure 2:
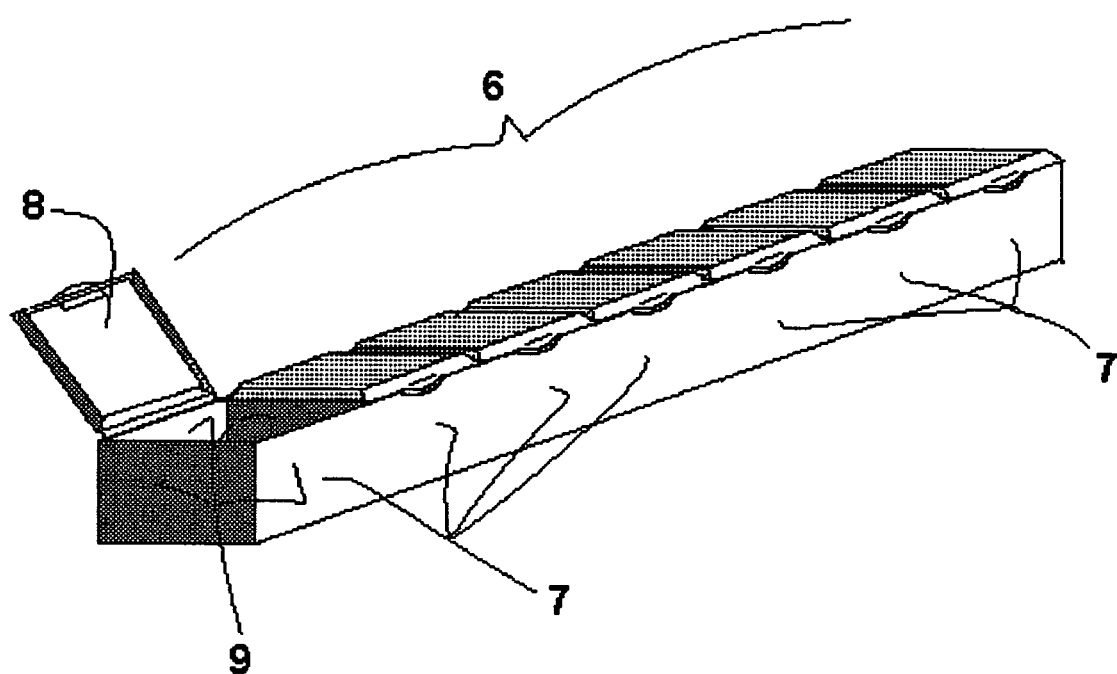
FIG. 2 is a perspective view of the compartmented elastic band container according to an illustrative, non-limiting embodiment of the present invention.

FIG. 2 shows a non-limiting representation of a compartmented container 6 that would be suitable for use with the new invention. The compartmented container depicted comprises seven compartments 7, one for each day of the week. Each compartment has associated with it, a lid 8, and a sufficient number of sides 9 to prevent the co-mingling of the contents of one compartment with the contents of another. Containers with more or less compartments would also work with the new method of orthodontic band regimen adherence verification. Any container which provides a plurality of individually accessible compartments, or compartments that would allow several elastic bands to be kept for each day, and such that the bands from each day do not intermingle, would be acceptable for use with the new system.

In general, a container with k compartments would be well-suited for determining whether an orthodontic patient has been compliant with their orthodontic elastic band regimen, for k days. Therefore, should $k=7$, as shown in FIG. 2, compliance with an elastic band regimen of up to one week would be supported based upon one inspection in accordance with the new method described in the following section. Verification of longer regimen would require determination based upon multiple inspections occurring no more than $k=7$ days apart. Should a container be available with 31 compartments, a regimen of one month of 31 days could be verified based upon one inspection of the container and the used elastic bands that it contains. Using a seven compartment container, compliance could be verified based upon four weekly inspections and one inspection after 3 days.

III. The Verification System:

The new system for verification of adherence to an orthodontic elastic band regimen is based upon the use and management of elastic bands dyed 2,3 with a semi-persistent food-based dye, such as those depicted in FIGS. 1B and 1C. The characteristic of the elastic bands that allows their signs of use to be self-evident to the person verifying the regimen makes the elastic bands suitable for use with the verification system. The new system is supported by use of a compartmented container 6 such as the one shown in FIG. 2. The compartmented container allows each day's used elastic bands 3 to be kept until such time as they can be accounted for in the process of verification.

Orthodontic regimens requiring the use of elastic bands typically involve the wearing of no more than five elastic bands at a given time. For purposes of further illustration, the number of elastic bands to be worn at any given time will be given the variable name "p". The regimen may require that the elastic bands are worn continuously, except for meals, or that the elastic bands be worn for a minimum number of hours each day. In any case, the number of elastic bands prescribed for use at any given time, taken with the number of hours per day that the elastic bands are to be worn, directly indicates a specific number of elastic bands that should be "consumed" during the course of a full day's prescribed regimen. The individual who seeks to verify the compliance with the regimen, must be aware of the number of elastic bands that are to be used each day. For the purposes of further illustration, the number will be assigned the variable name "n".

During the course of an orthodontic patient's typical day, elastic bands would typically be removed upon waking up and replaced with a set of p new bands subsequent to having breakfast and carrying out oral hygiene activities. The bands installed after breakfast would remain in place until lunchtime when they would be removed and replaced after dining. The process would be repeated for dinner time and for any additional meals or snacks throughout the day. For purposes of further illustration, the number of expected elastic band set replacements throughout the day will be assigned the variable name "m". Therefore, n, the total number of elastic bands to be used throughout the day would be given by pm, or the number of bands installed at any given time (p) multiplied by the number of elastic band changings per day (m).

Should the orthodontic patient be provided with the semi-persistently dyed elastic bands 2 and a compartmented container 6, and instructions to rinse and save each used elastic band 3, as it is removed, in the compartment 7 appropriate for the given day, the process of elastic band regimen adherence verification in accordance with the new system becomes a simple matter of verifying that at least n used bands are stored in each compartment up to the day of verification. If more than n used bands 3 are stored in a given compartment 7, the case that one or more bands were broken or an extra meal was enjoyed by the patient. In either event no deviation from the prescribed regimen would be indicated. Should less than n used bands 3 be provided in a given compartment 7, not including the current days compartment, depending upon the time of day that verification is taking place, it would be indicated would be that either used elastic bands 3 were used as opposed to new ones 2, or an insufficient number of elastic bands 2 were used during the course of that day, or a meal was skipped for that day. In all but the latter case, compromise of the prescribed elastic band regimen for that day would be indicated.

The new system allows for the number of days that a orthodontic patient fails to adhere to a prescribed regimen of orthodontic elastic band use to be determined based upon an accumulating inventory of identifiably used elastic bands throughout the period of the regimen under scrutiny. While the accuracy of the method is subject to certain assumptions regarding eating habits remaining predictable throughout the regimen period, the method would appear to be very useful for ascertaining the level of rigor with which an orthodontic patient is adherent to their elastic band regimen.

IV. An Illustrative Scenario:

The use verification system will be better appreciated by considering the following illustrative scenario, which is non-limiting. The parent of a juvenile orthodontic patient for whom the use of three elastic bands have been prescribed throughout the day purchases the elastic bands dyed in accordance with the new invention 2, and a seven compartment container 6. The juvenile orthodontic patient is instructed to remove all three elastic bands before each meal and to rinse and store them the container compartment to be used on each day. Further, the juvenile orthodontic patient is instructed to replace all three elastic bands removed, with new ones after each meal such that three elastic bands are being worn at all times with the exception of during meals and oral hygiene activities. The juvenile is provided with the unused elastic bands 2, and the compartmented container 6, on Monday morning, after breakfast and before school.

After school on Friday, the parent of the juvenile seeks to verify compliance with the elastic band regimen for the five days between Monday and Friday, inclusive. The juvenile presents the compartmented container 6. Lifting lid 8 for each of the five days since Monday. The parent counts a full complement of nine elastic bands in Monday's compartment. The elastic bands in the container show fading of color and localized retention of dye, both are signs of use. The parent has reason to conclude that adherence to the regimen was maintained on Monday. Only six used bands are stored in Tuesday's compartment. The juvenile explains that he forgot to replace his elastic bands after lunch and did not do so until after dinner. Wednesday's compartment contains eight used bands. The juvenile explains that one of the bands got lost while he was rinsing it. Thursday has a full complement of bands but three of the bands show very little, if any signs of wear. The juvenile explains that once again he had forgotten to replace his bands after lunch, but this time remembered to do so a short time prior to dinner. Six used bands are stored in Friday's compartment, which accounts for the sets removed after breakfast and lunch. The juvenile smiles and the third set, which will be removed before dinner, appear. The parent checks compliance for Friday night through Sunday night on Sunday night and disposes of the used elastic bands which were accumulated during the previous week.

The parent has successfully assessed the degree of rigor with which the child has been adherent to the prescribed orthodontic regimen over the preceding seven days. Such monitoring of the juvenile, by the parent will help the juvenile develop the care and maintenance habits required for a successful orthodontic treatment. The parent stands to save hundreds or thousands of dollars which might otherwise be spent due to extra orthodontic treatments which may not have been necessary had the elastic bands been used as prescribed. Once the juvenile establishes the habit of maintaining his orthodontic regimen faithfully, the parent can reduce the number of verifications or phase them out completely.

What is claimed is:

1. A method to verify adherence to an orthodontic elastic band regimen, the method comprising the steps of:
   providing elastic bands that have been dyed with a semi-persistent dye such that elastic bands which have been used are distnguishable from those that have not been used;
   providing a compartmented container which comprises a plurality of independently identifiable and accessible compartments;
   providing instruction to the orthodontic patient to retain each used orthodontic elastic band in a compartment of the container to be associated with a day, or period of time comprising a part of the overall regimen period;
   initiating an orthodontic elastic band regimen on a start date and in association with a starting compartment of the compartmented container;
   determining the rigor of adherence of the orthodontic elastic band regimen based upon the number of used elstic bands which have been stored in each compartment which is associated with a period of time comprising a part of the overall regimen period;
   determining a length of the orthodontic elastic band regimen, which extends from the start date corresponding to the last container compartment which contains a full complement of used elastic bands as determined by the number of bands to be worn at a given time and how many times per day the bands should be changed.

2. The method according to claim 1, wherein the period of time comprising a part of the overall regimen period is one day.

3. The method according to claim 1, wherein the orthodontic elastic band regimen involves the replacement of a full complement of elastic bands after each meal of the day.

4. The method according to claim 1, wherein the orthodontic elastic band regimen involves the replacement of a full complement of elastic bands on a daily basis.

* * * * *